United States Patent [19]

Damon, II et al.

[11] Patent Number: 4,829,081
[45] Date of Patent: May 9, 1989

[54] ANALOGS OF MEVALONOLACTONE AND DERIVATIVES THEREOF

[75] Inventors: Robert E. Damon, II, Wharton; James R. Wareing, Randolph, both of N.J.

[73] Assignee: Sandoz Pharm. Corp., E. Hanover, N.J.

[21] Appl. No.: 945,428

[22] Filed: Dec. 22, 1986

Related U.S. Application Data

[63] Continuation-in-part of Ser. No. 816,664, Jan. 7, 1986, abandoned.

[51] Int. Cl.$^4$ .............................................. A61K 31/38
[52] U.S. Cl. ...................... 514/438; 549/60; 549/79; 549/292; 549/454; 514/444; 514/460; 514/461
[58] Field of Search .................. 549/79; 514/438, 406

[56] References Cited

U.S. PATENT DOCUMENTS 4,379,158  4/1983  Hirata et al. .................. 514/438
4,613,610  9/1986  Wareing .......................... 548/374

Primary Examiner—Glennon H. Hollrah
Assistant Examiner—Amelia Owens
Attorney, Agent, or Firm—Gerald D. Sharkin; Richard E. Vila; Joanne M. Giesser

[57] ABSTRACT

Compounds of the formula

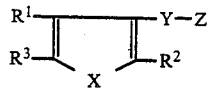

in which Y is

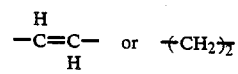

X is O or S;
Z is —CHOH—CH$_2$—CHOH—CH$_2$—COOH, an ester or salt thereof or the lactone thereof; and
each of R$^1$, R$^2$ and R$^3$ can be alkyl, cycloalkyl; or substituted or unsubstituted phenyl; and additionally R$^3$ can be hydrogen, are obtained by a multistep process and are useful in the treatment of atherosclerosis, e.g. sodium(E)-7-(4-phenyl-2-isopropyl-5-phenylthien-3-yl)-3,5-dihydroxyhept-6- enoate.

15 Claims, No Drawings

ANALOGS OF MEVALONOLACTONE AND DERIVATIVES THEREOF

This is a continuation-in-part of application Ser. No. 06/816,664 (filed Jan. 7, 1986) now abandoned.

This invention relates to organic compounds, and more specifically to thienyl-and furanyl-substituted lactones and thienyl-and furanyl-substituted-dihydroxyacids and their ester and salt derivatives; to pharmaceutical compositions containing such compounds; and to the use of such compounds; as well as to intermediates in the preparation of such compounds.

The final compounds of this invention may conveniently be represented by formula I:

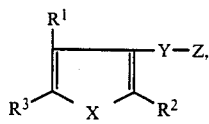
(I)

wherein $R^1$ is $C_{1-6}$alkyl not containing an asymmetric carbon atom, $C_{3-7}$cycloalkyl or ring A

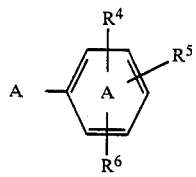

wherein $R^4$, $R^5$ and $R^6$ are as defined below,
$R^2$ is $C_{1-6}$alkyl not containing an asymmetric carbon atom, $C_{3-7}$cyloalkyl or ring B:

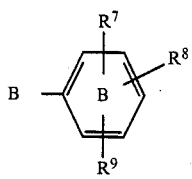

wherein $R^7$, $R^8$ and $R^9$ are as defined below,
$R^3$ is hydrogen, $C_{1-6}$alkyl not containing an asymmetric carbon atom, $C_{3-7}$cycloalkyl or ring C:

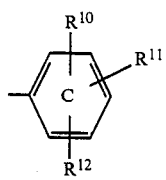
C wherein $R^{10}$, $R^{11}$ and $R^{12}$ are as defined below:
Y is (a)

or (b) $-CH_2-CH_2-$;
X is $-O-$ or $-S-$; and

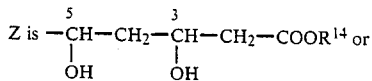
(a)

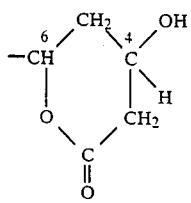
(b)

$R^{14}$ is hydrogen, $R^{15}$ or M,
 wherein
  $R^{15}$ is a physiologically acceptable ester group, and
  M is a pharmaceutically acceptable cation,
wherein each of $R^4$, $R^7$ and $R^{10}$ is independently hydrogen,
 $C_{1-3}$alkyl, n-butyl, i-butyl, t-butyl,
 $C_{1-3}$alkoxy, n-butoxy, i-butoxy, trifluoromethyl, fluoro, chloro, phenyl, phenoxy or benzyloxy,
 each of $R^5$, $R^8$ and $R^{11}$ is independently hydrogen, $C_{1-3}$alkyl, $C_{1-3}$alkoxy, trifluoromethyl, fluoro, chloro, phenoxy or benzyloxy,
 each of $R^6$, $R^9$ and $R^{12}$ is independently hydrogen, $C_{1-2}$alkyl, $C_{1-2}$alkoxy, fluoro or chloro, with the provisos that not more than one substituent on each of Rings A, B and C, independently is trifluoromethyl, not more than one substituent on each of Rings A, B and C, independently is phenoxy, not more than one substituent on each of Rings A, B, and C independently is benzyloxy, ie
 each of rings A, B and C bears no more than one of trifluoromethyl, phenoxy or benzyloxy radicals;
in addition, when Y is (a), $R^3$ may be

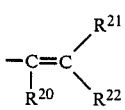

in which $R^{20}$ is hydrogen or $C_{1-3}$alkyl; and $R^{21}$ and $R^{22}$ are, independently, hydrogen, $C_{1-3}$alkyl or phenyl (eg methyl, preferably $R^{21}$ and $R^{22}$ being the same).

Compounds I may be further viewed as consisting of two classes, depending upon whether Z is of formula (a) or (b), ie:

$$Q-Y-CHOH-CH_2-CHOH-CH_2-COOR^{14} \text{ and} \quad \text{Ia}$$

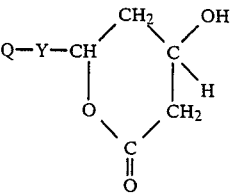
Ib wherein Y and $R^{14}$ are as defined above and Q is the unit:

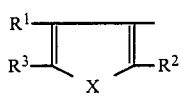

wherein $R^1$, $R^2$, $R^3$ and X are as defined above.

In addition compounds Ia may be viewed as belonging to three subclasses depending upon the nature of $R^{14}$ ie:

$$Q-Y-CHOH-CH_2CHOH-CH_2-COOR^{15} \qquad Ia^1$$

$$Q-Y-CHOH-CH_2-CHOH-CH_2-COOM, \text{ and} \qquad Ia^2$$

$$Q-Y-CHOH-CH_2CHOH-CH_2-COOH \qquad Ia^3$$

wherein $R^{15}$, M and Q are defined above.

It will be appreciated that compounds $Ia^1$, $Ia^2$, $Ia^3$ and Ib can be interconverted by conventional means in the art. For example a compound $Ia^3$ can be lactonized to form the corresponding compound Ib. Likewise a compound $Ia^1$ or Ib can be saponified to its corresponding compound $Ia^2$ which can in turn be esterified to a compound $Ia^1$ or neutralized, eg by treatment with an acid, to form its corresponding compound $Ia^3$.

The above-described interconversions are conveniently represented in Reaction Scheme A, below, wherein Q, Y, M, $R^{13}$ and $R^{15}$ are as defined above.

For example, lactonization of a compound $Ia^3$ (process) (m) is accomplished by heating a compound $Ia^3$ (in which $R^{14}=H$) in an inert medium, e.g. an aromatic hydrocarbon, such as toluene, at from about 80° to 140° C., for example at the reflux temperature of the reaction medium; or by treating with 1-cyclohexyl-3-(2-morpholinoethyl)-carbodiimide methyl p-toluene sulfonate in an inert medium, eg methylene chloride ($CH_2Cl_2$), at moderate temperatures, eg 20° to 40° C.

Saponification of a compound $Ia^1$ or Ib (process m') to obtain a corresponding compound $Ia^2$, is achieved by treatment with aqueous alkali metal base, e.g. sodium hydroxide, preferably in a water-miscible co-solvent, e.g. ethanol or dioxane, at, e.g. from about 0° to 100° C., particularly about 25° to 60° C. Where a product is desired in which $R^{14}$ is hydrogen, i.e., the free acid form, (a compound $Ia^3$) such is obtained by acidifying the salt form (where $R^{14}=M$) by conventional means, e.g. by addition of dilute hydrochloric acid (process n).

Esterification according to m" is conventional employing e.g. a large excess of a compound $R^{15}-OH$ wherein $R^{15}$ is as defined above, at 20° C. to 40° C. optionally in a solvent (especially when $R^{15}-OH$ is not liquid) and in the presence of a catalytic amount of an acid such as p-toluenesulfonic acid. Where methyl esters are required these can also be obtained e.g. using diazomethane in an anhydrous inert ether solvent such as tetrahydrofuran (THF).

Reaction Scheme A

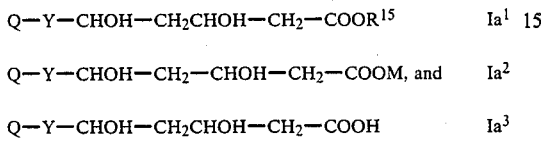

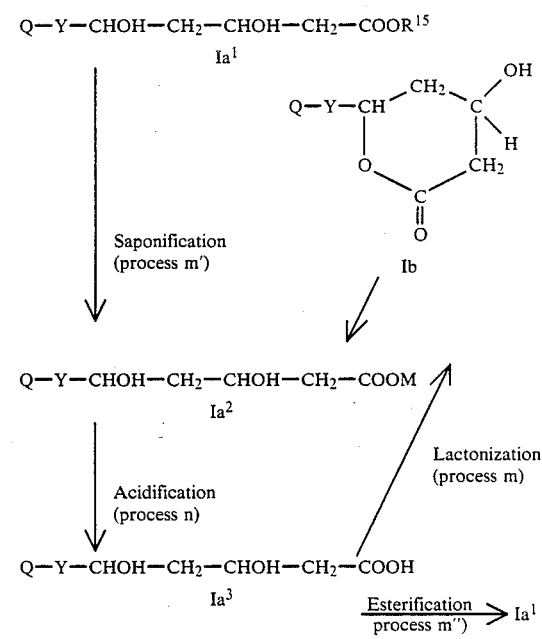

Compounds $Ia^1$ in which Y is an olefinic group of type (a) are conveniently obtainable by a series of reaction steps starting with a 3-carboalkoxy compound of formula A:

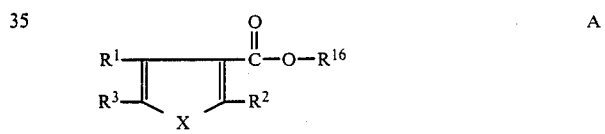

wherein X, $R^1$, $R^2$ and $R^3$ are as defined above, and $R^{16}$ is unbranched lower alkyl (1–4C) preferably ethyl; by a series of reaction steps which are conveniently represented by Reaction Scheme B, below, in which $R^1$, $R^2$, $R^3$, Q, X, $R^{15}$ and $R^{16}$ are as defined above; Et is ethyl and Ak is an equivalent of an alkaline metal, eg Li, Na or K, preferably Li.

REACTION SCHEME B

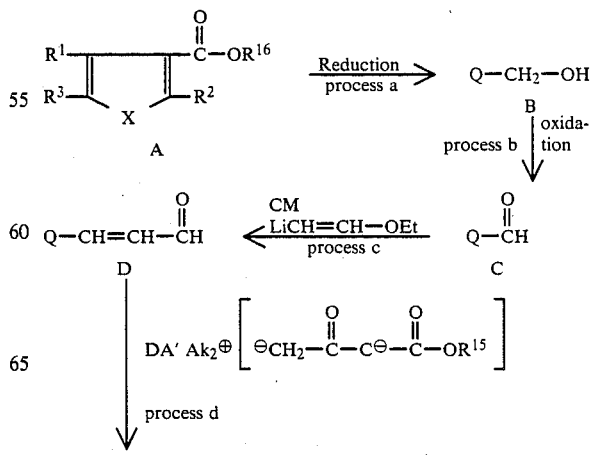

REACTION SCHEME B
-continued

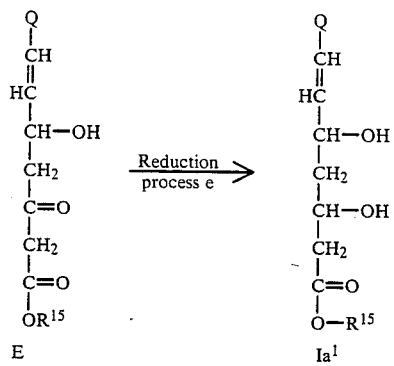

In process (a) the ester unit on a compound A is reduced to a hydroxymethyl unit, to form a compound B. The reduction may be accomplished by conventional methods for carrying out such a reduction. A convenient method is to employ lithium aluminum hydride (LAH) at moderate temperatures eg 20° to 85°, such as room temperature or refluxing temperatures, in an inert medium eg an ether such as diethyl ether or THF, under essentially anhydrous conditions.

In process (b) the hydroxymethyl unit on a compound B is oxidized to an aldehydic function to form a compound C. The oxidation may be accomplished by conventional means for accomplishing such a reaction, eg by a Swern procedure or by employing N-methylmorpholine N-oxide (NMO) and a catalytic amount of tris(triphenylphosphonium) ruthenium dichloride, ie $(P(C_6H_5)_3)_3RuCl_2$, in an inert medium, eg acetone at moderate temperatures eg 15° to 50°; eg room temperatures, under essentially anhydrous conditions, preferably in a molar ratio of NMO: compound A of about 2:1.

Process (c) is an addition reaction in which a lithium salt of formula CM:

$$CM \quad Li^{\oplus}[CH=CH-OC_2H_5]^{\ominus}$$

is reacted with a compound C to form the corresponding compound D, under essentially anhydrous conditions, in an inert medium eg a cyclic ether, such as THF, at reduced temperatures, eg −70° to −80° C., particularly at −78° C., followed by quenching in an aqueous acidic medium.

The reagent CM is obtainable by reacting a lithium source, eg an organometallic agent, such as tert.-butyl lithium in an inert medium at reduced temperatures eg −80° to 0° C., under anhydrous conditions, with a vinyl ether of the formula CM'

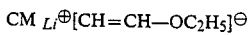

in an inert medium, eg a cyclic ether, such as THF, under essentially anhydrous conditions. Preferably, the reagent CM is used in situ, the medium in which it was prepared, also serving as the reaction medium.

Process (d) is also an addition reaction. The process comprises three steps. First, an alkali metal-dianion (DA') is formed eg. by treating a compound DA (an $R^{15}$-ester of acetoacetic acid), under essentially anhydrous conditions, with sodium hydride, and then a strong base, eg n-butyl lithium, or with lithium diisopropylamide (LDA) in an inert organic medium, eg a cyclic ether, such as THF, at reduced temperatures eg −25° to 5° C., such as −15° C. The resultant reagent (DA') is then reacted, still under essentially anhydrous conditions, with a compound D, at reduced temperatures, eg about −25° to 5° C., such as −15° to −20° C. in an inert medium, eg a cyclic ether, such as THF, to form an addition product. The addition product is then hydrolyzed by treatment with an aqueous agent eg. water to yield the corresponding compound E. Since DA' is a dianionic salt, at least 2 equivalents of the strong base, eg 2 to 2.2 are employed in the first step. It is convenient to react reagent DA' in situ.

Process (e) is a mild reduction and may be accomplished in the conventional manner for reducing a ketone to a secondary alcohol. An alternative method of accomplishing process (e) is a three step process which involves first treating a compound E with a trialkyl borane (process e'), then treating the reaction mixture with sodium borohydride to obtain a complex (process e'') and then cleaving the complex by treating the product with methanol (process e'''), to obtain the corresponding diol ester compound $Ia^1$.

Process (e') is carried out under anhydrous conditions. The alkyl groups of the trialkyl borane may have 2 to 4 carbon atoms and be primary or secondary, eg triethyl borane. Preferably an excess of the trialkylborane per mole of compound E, is employed in this step. Air may also be employed but is not essential. The reaction is carried out in an organic medium, eg a cyclic ether such as THF or a mixture of THF and methanol, at moderate temperatures, eg at about 0° to +30° C., eg about +20° to +30° C. The reaction mixture is cooled, eg to about −100° to −40° C., especially −78° C., and sodium borohydride (NaBH4) added thereto; the solvent and essentially anhydrous conditions employed in process E' being maintained. After sufficient reaction time, the temperature of the mixture is allowed to rise, and then quenched with an aqueous agent, eg water, and the product (complex) recovered and refined as desired. In (process e''') the product of (process e'') is treated with a large excess of methanol at moderate temperatures, eg +20° to +80° C., under essentially anhydrous conditions, to obtain the corresponding compound $Ia^1$.

Process (e) in general gives a mixture of *erythro* and *threo* isomers. Where a high proportion of *erythro* form is desired, the three step process is preferably employed. Use of the mixed medium eg THF: methanol (3–4:1) also favors high yields of the *erythro* isomer.

Alternatively to the portion of Reaction Scheme B illustrating the preparation of a compound D from a corresponding compound C, compounds C may be prepared by the series of reaction steps represented in Reaction Scheme C, below, in which Q and Et are as defined above and Ak' is an equivalent of an alkali metal cation, eg. Li, Na or K, preferably Li.

REACTION SCHEME C

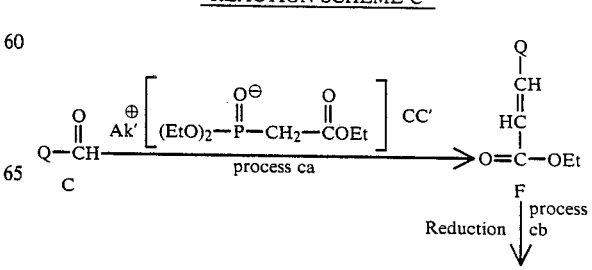

-continued
REACTION SCHEME C

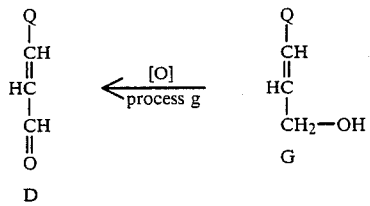

-continued
REACTION SCHEME D

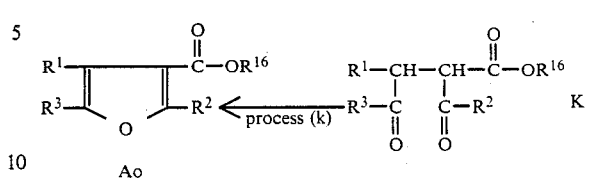

The alternative procedure for converting a compound C to a corresponding compound D, is via processes (ca) plus (cb). A compound F is obtained by reacting a compound C, with a reagent of formula CC' in an inert medium, eg an ether, such as THF or ether, at moderate temperatures eg from about 10° to 80°, eg RT, under anhydrous conditions.

Reagents CC' are obtainable by reacting a compound CC of the formula CC:

in which Et is ethyl, with an alkali metal strong base, eg a hydride such as NaH when Ak'=Na, at reduced temperatures eg −10° to +5° C., eg 0°, under essentially anhydrous conditions, in an inert medium, eg a cyclic ether, such as THF. The reaction may be initiated cautiously at room temperature and then the temperature lowered. It is preferred to use the thus-prepared reagent CC' in situ, with the same medium serving for the preparation of the reagent, as well as process ca.

Reduction of a compound F to its corresponding compound G (process cb) may be accomplished in the conventional manner for reducing an ester to its corresponding primary alcohol, eg by adaption of the procedure of process (a); preferably employing DIBAL, in diethyl ether at −78° C. The resultant alcohol G may be oxidized to it corresponding aldehyde (D) by conventional means, eg by adaption of the procedure of process (b), described above.

Compounds A are either known and may be prepared as described in the literature or where not known may be prepared by methods which are analogous for the preparation of known compounds.

Compounds A in which X is O, ie compounds Ao may be prepared by a series of reaction steps as represented in Reaction Scheme D, below, in which $R^1$, $R^2$, $R^3$ and $R^{16}$ are as defined above.

REACTION SCHEME D

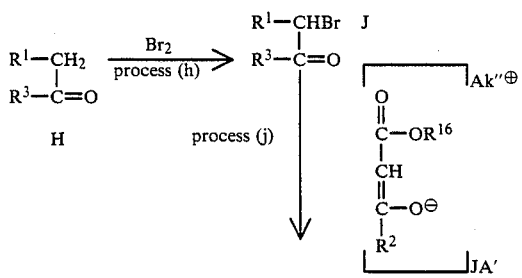

In process (h), a ketone bearing the moieties $R^1$ and $R^3$ is brominated to form a corresponding compound J in which a hydrogen atom of a compound H is replaced by a single bromine atom. Bromine is preferably supplied by liquid bromine. The reaction is conveniently carried out in an inert medium, eg a halogenated hydrocarbon, such as chloroform ($CHCl_3$), at moderate temperatures, eg 0° to 40° C. eg R.T., although it is preferable to initiate the reaction at room temperature by adding a few drops of bromine, cool to about 0° C., add the remaining charge dropwise, then allow the mixture to warm to run to completion.

Process (j) is an addition reaction, in which a bromocompound (J) is reacted with reagent (JA'), under essentially anhydrous conditions, at moderate temperatures, eg from 10° to 40° C., such as at RT, in an inert medium, eg a cyclic ether such as THF. It is preferable to initiate the reaction at low temperatures, eg 0° C. and then allow the temperature to rise eg to RT.

Reagents JA' are obtainable by forming an alkali salt of a keto-ester of formula JA:

in which $R^2$ and $R^{16}$ are as defined above, by reaction with a strong alkali metal base, eg a hydride when Ak" is Na, under essentially anhydrous conditions, in an inert organic medium eg a cyclic ether, such as THF, at reduced temperatures eg from about −10° to +5° C., particularly at about 0° C. It is preferred to use compounds JA' in situ, thus the same medium and conditions serve for both the preparation of a compound JA' and process (j) to obtain the corresponding compound K.

Process (k) involves the cyclization of a compound K to form its corresponding compound Ao. Process (k) is conveniently accomplished by treating a compound K with boron trifluoride diethyl etherate, at eg 80° to 140° C., such as reflux temperature of the reaction mixture, in an inert organic medium, eg a hydrocarbon such as toluene or xylene, followed by quenching with an aqueous solution, eg aqueous sodium bicarbonate. The boron trifluoride complex is preferably present in a molar excess of about 2 to 8: mol of compound K.

Compounds As in which $R^3$ is aryl are obtainable by treating a corresponding compound K, defined above, by methods known in the art, such as $P_2S_5$, or with "Lawesson's Reagent".

A convenient method of obtaining compounds As', ie compounds As in which $R^3$ is $R^{3'}$=phenyl, or p=methyl- or p-methoxyphenyl, is a multi-step procedure which may be represented by Reaction Scheme E, below in which $R^1$, $R^2$, $R^{3'}$, $R^{16}$ and Q are as defined above.

REACTION SCHEME E

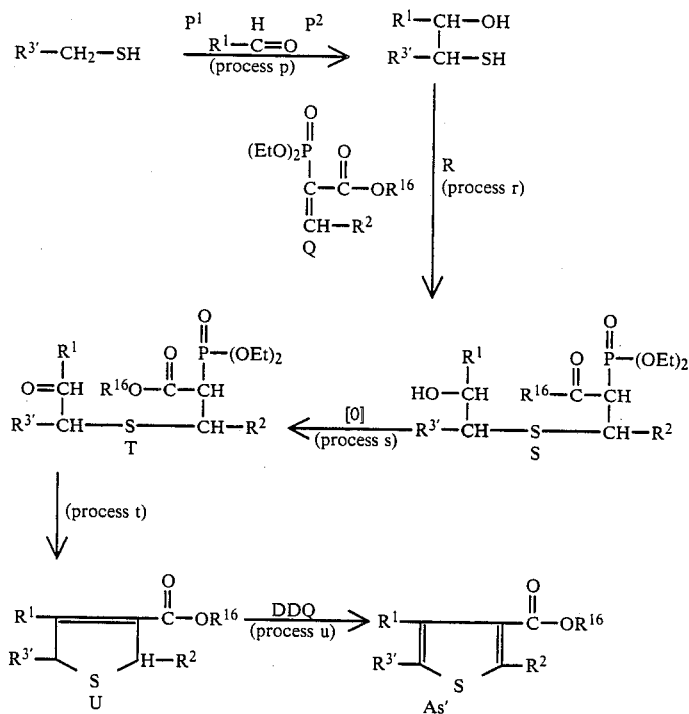

Process (p) shown in Reaction Scheme (E), above, is an addition reaction. It consists of two stages; first an alkali metal salt (ie Li, K or Na) of a compound $P^1$ (bearing $R^1$) is prepared, which is then reacted with an aldehyde bearing the $R^3$ moiety, ie a compound $P^2$. The first stage is accomplished by treating a compound $P^1$ with an alkali metal strong base, such as n-butyl lithium in an inert organic medium, eg a cyclic ether, such as THF, at reduced temperatures, eg $-10°$ to $+10°$ C., such as about $0°$ C. Both the first and second stages are carried out under essentially anhydrous conditions. The thus-prepared alkali metal salt of compound $P^1$ is then reacted preferably in situ with a compound $P^2$ preferably in the same medium as used in the first stage at reduced temperatures, eg $-30°$ to $-15°$ C., eg about $-25°$ C. The reaction is then quenched with an aqueous agent, eg saturated aqueous ammonium chloride, to obtain the corresponding compound R.

In process (r), a compound R is treated with an appropriate reagent Q in an inert organic medium, eg a cyclic ether, such as THF, at moderate temperatures eg $15°$ to $60°$ C., such as R.T., in the presence of a acid neutralizing agent, eg a tertiary amine, such as triethylamine to obtain the corresponding compound S. The molar ratio of R to Q is preferably about 1:1, with about 10% molar excess of the neutralizer present.

In process (s), the hydroxymethyl unit is oxidized to an carbonyl function. The oxidation may be carried out by conventional means. A convenient method of carrying out the oxidation is by the Swern procedure, i.e., by treating a compound with the reagent formed by oxalyl chloride, and dimethyl sulfoxide at reduced temperatures, e.g., about $-90°$ to $-40°$ C., e.g., about $-65°$, in an inert medium e.g., a chlorinated hydrocarbon; such as ethylene chloride or methylene chloride, under essentially anhydrous conditions, then adding triethylamine and allowing the reaction mixture to warm, e.g. to $20°$ to $70°$, such as R.T., then quenching the reaction mixture with an aqueous agent, e.g. water.

Process (t) is a cyclization. It may be accomplished by treating a compound T with a strong base, eg lithium diisopropylamide, in an inert organic medium, eg a cyclic ether, such as THF, at reduced temperatures eg $-10°$ to $+5°$ C., e.g. about $0°$ C., under essentially anhydrous conditions, then hydrolyzing the resultant reaction product by treatment with an aqueous reagent, e.g. aqueous $NH_4Cl$ solution, to obtain the corresponding compound U.

In process (u) thus, the dihydro-thienyl nucleus of a compound u is "aromatized", ie it is converted to a thienyl nucleus, to provide the corresponding compound As'. A compound U may be "aromatized", by treatment with DDQ, ie 2,3-dichloro-5,6-dicyano-1,4-benzonquinone in an organic medium, eg a chlorinated hydrocarbon, such as methylene chloride, or an ether, such as tetrahydrofuran, at moderate temperatures, eg at from about $20°$ to $40°$ C., preferably at room temperature.

A method of preparing compounds As in general and which is especially preferred for preparing compounds As", i.e. compounds A in which $X=S$, and $R^3=R^{3''}$ i.e. it is the same as $R^3$ when it is not phenyl, i.e. it is hydrogen, alkyl, cycloalkyl or substituted phenyl, is conveniently represented by Reaction Scheme F in which $R^1$, $R^2$, $R^3$, $R^{16}$ and Et are as defined above.

REACTION SCHEME F

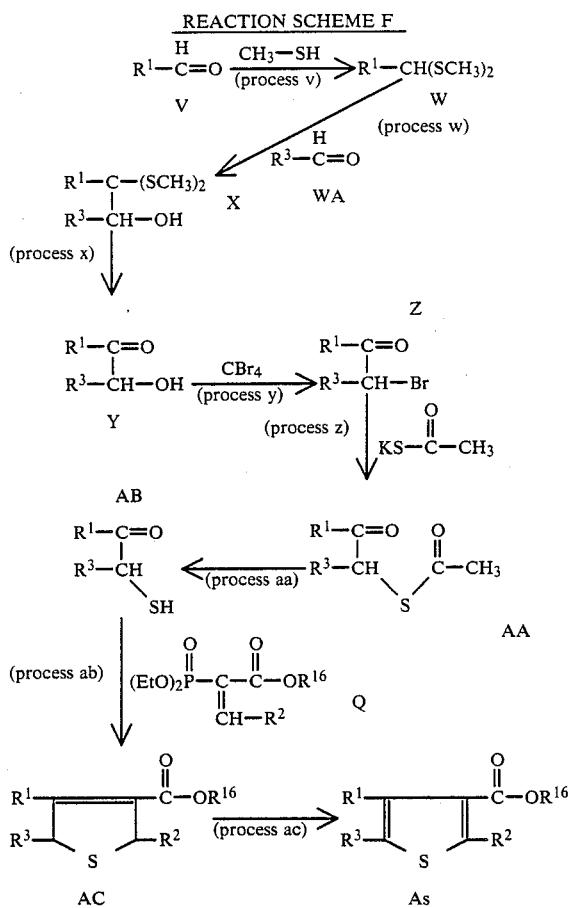

In the procedure of Reaction Scheme F, in process (v) an $R^1$-aldehyde, ie a compound V is reacted with two equivalents of methanethiol ($CH_3SH$) in an inert medium, e.g. ether, at reduced temperatures e.g. $-10°$ to $+5°$ C., e.g. about $0°$ C., in the presence of $BF_3\cdot(C_2H_5)_2O$, i.e. boron trifluoride diethyl etherate, and the resulting intermediate product hydrolzyed by quenching with a basic aqueous solution, e.g. dilute aqueous sodium hydroxide to obtain the corresponding compound W. Since two moles of methanethiol a reacted per mol of aldehyde (V), it is preferable to have these reactants present in a ratio of methanethiol to compound V of at least 2:1.

Process (w) is an addition reaction and consists of 3 stages. First a compound W is treated with a strong alkali metal base, eg n-butyl lithium to form a alkali salt of the dithioketal (W) at reduced temperatures e.g. $-80°$ to $-60°$ C., e.g. about $-78°$ C. in an inert medium e.g. a cyclic ether, such as THF, under anhydrous conditions.

In the second stage the thus-formed alkali-metal salt is reacted in situ with a $R^3$-aldehyde (a compound WA), hence the same medium and conditions are employed, and at the same temperatures to form in situ a reaction product. The reaction product is then hydrolyzed by quenching with an aqueous agent, e.g. saturated aqueous ammonium chloride, to obtain a corresponding hydroxydithioketal (X).

Process (x) may be viewed as a conversion of a hydroxy dithioketal (X) to its parent ketone (Y). This is accomplished by treating a compound X with mercuric oxide (red) in the presence of $BF_3\cdot(C_2H_5)_2O$ in an inert organic medium e.g. a cyclic ether, such as THF, at reduced temperatures, e.g. $-10°$ to $+5°$ C., such as $0°$ C.

Process (y) is a bromination, and may be accomplished in the conventional manner for converting a secondary alcohol (Y) to its bromo analog. For example, by reacting with carbon tetrabromide and triphenyl phosphine at moderate temperatures e.g. $20°$ to $60°$ C., such as R.T., in an inert organic medium, e.g. a cyclic ether such as THF, to obtain the corresponding ketobromide (Z).

In process (z) a ketobromide (Z) is converted to its corresponding thioacetate (AA), by reacting with potassium thioacetate in an inert medium, eg a lower alkanol, such as ethanol, under essentially anhydrous conditions, at moderate temperatures eg $20°$ to $50°$ C., such as R.T.

In process (aa) a thioester (AA) is converted to its parent mercaptan, by treating with a strong acid, eg concentrated hydrochloric acid, at moderate temperatures, eg $20°$ to $80°$ C., such as $60°$ C., in an inert polar medium, eg a lower alcohol, such as methanol.

In process (ab), an alkali metal salt of a mercaptoketone compound (AB) is reacted with an $R^2$ bearing-phosphate ester reagent of the formula Q:

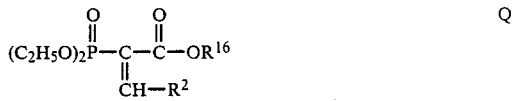

in which $R^2$ and $R^{16}$ are as defined above to form a corresponding dihydrothienyl compound (AC).

First a compound AB is treated with an alkali-metal strong base to form the corresponding alkali-metal salt of a compound AB, eg by employing lithium diisopropylamide in an inert organic medium, e.g. a cyclic ether, such as THF, at reduced temperatures, e.g. $0°$ C., under essentially anhydrous conditions.

The thus-obtained alkali-metal salt is then reacted in situ with a reagent (Q) at a reduced temperatures, e.g. $-80°$ to $-60°$ C., such as $-78°$; the medium and conditions for the first stage being also employed for the second stage to form a reaction product which is then hydrolyzed to obtain the corresponding compound AC by quenching with an aqueous agent, e.g. saturated aqueous ammonium chloride.

The resultant compound AC may then be "aromatized" to its corresponding compound As" by adaptation of process (u), described above in connection with the preparation of compounds Ao'.

Compounds I or intermediates thereof (in which Y is b), i.e. an ethylene unit, may be obtained from their corresponding compounds I in which Y is of type (a), by conventional means for converting an olefinic unit into an ethylene unit, e.g. by hydrogenating in the presence of a catalyst, such as platinum oxide or palladium on a carrier such as carbon at a pressure of e.g. 30 to 70 psi; caution being exercised where substituents are present which are susceptable to alteration by reduction in order to selectively reduce the olefinic unit. A particularly convenient point at which to carry out such conversion is on compounds E or $Ia^1$ in which Y is of type (a).

Reagents and starting materials described herein, e.g. compounds CC, H, JA, CM, DA, $P^1$, $P^2$ and AD are known and obtainable by known means, or where not known, may be obtained by adaptation of methods reported in the literature for the preparation of known analogs; some compounds being commercially available.

The final products and intermediate compounds described herein may be recovered and refined, where such is desired, by conventional means, such as by crystallization, distillation or chromatographic techniques such as column or thin layer chromatography, e.g. silica gel column chromatography.

Evaporations are done under vacuum employing minimal heating. Drying of organic phases is done over anhydrous sodium sulfate, unless indicated otherwise.

By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein $R^{14}$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl.

It will be noted that when Y of type (a), the moiety Z is in trans relationship to the furanyl or thienyl nucleus. It is preferred that when Z is of type b, i.e. when Z is a lactone ring, that the 6-hydrogen atom be in trans relationship to the 4-hydrogen. Such trans lactone-moiety can be formed when the 3- and 5-hydroxy functions on the 3, 5-diol-ester moiety (a), are in erythro relationship.

As is self-evident to those in the art, each compound of Formula I (and every subscope and species thereof) has two centers of asymmetry (the two carbon atoms bearing the hydroxy groups in the group of Formula a) and the carbon atom bearing the hydroxy group and the carbon atom having the free valence in the group of Formula b) and, therefore, there are four stereoisomeric forms (enantiomers) of each compound (two racemates or pairs of diastereoisomers), provided that M or $R^{15}$ do not contain any center of asymmetry. The four stereoisomers may be designated as the R, R; R, S; S, R and S, S enantiomers, all four stereoisomers being within the scope of this invention.

As will be understood, a racemic threo 3, 5-dihydroxycarboxylic acid yields a racemic cis lactone and a racemic erythro 3, 5-dihydroxycarboxlic acid yields a racemic trans lactone. Use of a mixture of threo and erythro 3, 5-dicarboxylic acid yields a mixture of cis and trans lactones (all four possible diastereoisomers). Likewise if a single enantiomer of the 3, 5-dihydroxycarboxylic acid is utilized, a single enantiomer of the lactone is obtained. For example, lactonisation of 3R, 5S erythro dihydroxycarboxylic acid yields a 4R, 6S isomer.

Mixtures of stereoisomers (cis, trans and optical) may be separated by conventional means at whatever stage of synthesis is appropriate. Such methods include recrystallization, chromatography, formation of esters with optically pure acids and alcohols or of amides and salts (cf also Sommer et al. J. A. C. S. 80, 3271 (1985) with subsequent reconversion under retention of optical purity.

The generally preferred compounds of this invention have one or more of the following characteristics:

Y is of type (a);
X is S;
Z is of type (a);

that there be a minimum number of asymmetric centers present;
the 3- and 5-hydroxy groups be in erythro relation to each other;
in compounds I $R^{14}$=M, i.e. it be in a salt form, especially a sodium salt;
when $R^{14}$=$R^{15}$ it is ethyl;
$R^2$ is alkyl, especially isopropyl or tert.-butyl; and
$R^1$ or $R^2$ be phenyl or p-substituted phenyl, e.g. p-fluorophenyl.

UTILITY

Besides having the utility set forth below, every compound of Formula I is useful as an intermediate in the synthesis of one or more other compounds of Formula I utilizing the reactions set forth in Reaction Scheme A, above.

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates such as humans, and, therefore, as hypolipoproteinemic and anti-atherosclerotic agents. The biological activity of the compounds of Formula I may be demonstrated in the following two tests:

Test A.

In Vitro Microsomal Assay of HMG-CoA Reductase Inhibition

This test is carried out precisely as described in column 53 of U.S. Pat. No. 4,613,610 and on page 30 of World (PCT) Published patent application 84/02131, both of which are hereby incorporated by reference as if set forth herein in their entirety. The concentration of the test substance (compound of Formula I) in the assay system is 0.0005–2,000 μmolar. The obtained $IC_{50}$ is the concentration of the test substance in the assay system observed or calculated to produce a 50% inhibition of HMG-CoA reductase activity.

Test B.

In Vivo Cholesterol Biosynthesis Inhibition Test

This test is carried out precisely as described in column 53 of said U.S. Pat. No. 4,613,610 and on page 33 of World (PCT) Published patent application 84/02131, both of which are hereby incorporated by reference as if set forth herein in their entirety. In this test the rats are orally administered the test substance (compound of Formula I) at dose of 0.01–200 mg/kg. body weight. The obtained $ED_{50}$ is the dose of the test substance observed or calculated to produce a 50% inhibition of 3β-hydroxysterol synthesis.

In Test A, tested compounds of Formula I had $IC_{50}$'s of about 0.003 to >10 μmolar whereas that of Compactin was 1.01 μmolar and that of Mevinolin was 0.14 μmolar. The preferred compounds of this application, those of Examples 5b, 5c and 8 (sodium salt) had $IC_{50}$'s of 0.190, 0.028 and 0.027 μmolar respectively. In Test B, tested compounds of Formula I had $ED_{50}$'s of about 0.08 to >1.2 mg./kg. whereas that of Compactin was 3.5 mg./kg. and that of Mevinolin was 0.41 mg./kg. The $ED_{50}$'s of the preferred compounds, that of Examples 5b, 5c and 8 (sodium salt) were 0.35, 0.169 and 0.076 mg./kg., respectively.

The precise dosage of the compound of Formula I to be employed for inhibiting cholesterol biosynthesis depends upon several factors including the host, the nature and the severity of the condition being treated, the mode of administration and the particular active substance (compound of Formula I) employed. However, in general, suitable oral daily dosages of the compounds of Formula I for the satisfactory inhibition or reduction of cholesterol biosynthesis (i.e., the satisfactory reduction of blood cholesterol level and satisfactory treatment of hyperlipoproteinemia and atherosclerosis) are indicated by the test data to be from about 0.03 to 100 mg./kg. body weight, e.g., 0.03 to 6 mg./kg. body weight for the more active compounds. For most larger primates such as humans, a suitable oral daily dosage is indicated to be from about 1 to 2,000 mg., e.g., from about 1 to 150 mg. especially from about 4 to 40 mg. for the more active compounds. For administration by injection, a dosage somewhat lower than would be used for oral administration of the same active substance to the same host having the same condition is usually employed. However, the above dosages are also typically used for i.v. administration.

The daily dosage may be administered in a single dose but more typically is administered in two to four equal portions, typical doses being from about 0.25 to 1,000 mg. especially from about 0.25 to 150 mg. Often, a small dosage is administered initially, and the dosage is gradually increased until the optimal dosage for the host under treatment is determined.

A typical dosage unit for oral administration of the more active compounds may contain from about 0.25 to 75 mg. of a compound of Formula I.

With particular respect to the class of compounds I, in which X is oxygen, ie compounds Io, the following is applicable:

The daily dosage may be administered in a single dose more typically is administered in two to four equal portions, typical doses being from about 3 to 150 mg. A typical dosage unit for oral administration may contain from about 0.75 to 75 mg. of a compound of Formula Io.

With particular respect to the class of compounds I, in which X is sulfur, i.e. compounds Is, the following is applicable:

The daily dosage may be administered in a single dose but more typically is administered in two to four equal portions, typical doses being from about 1 to 75 mg. especially about 4 to 40 mg. A typical dosage unit for oral administration may contain from about 0.25 to 38 mg. especially about 1 to 10 mg. of a compound of Formula Is.

The compounds of Formula I may be formulated into conventional pharmaceutical compositions and administered by any conventional mode of administration, in particular enterally, e.g., in the form of capsules or tablets, or parenterally, e.g., in the form of sterile injectable solutions or suspensions. The pharmaceutical compositions comprise a compound of Formula I and at least one pharmaceutically acceptable solid or liquid carrier (or diluent). They may be formulated in conventional manner. The compounds of each subgroup thereof may likewise be formulated into such pharmaceutical compositions and administered by such routes.

The compounds of Formula I (including those of each subgroup thereof) may be formulated into such pharmaceutical compositions containing an amount of the active substance that is effective for inhibiting cholesterol biosynthesis in unit dosage form and such compositions comprising at least one solid pharmaceutically acceptable carrier.

Representative formulations suitable for encapsulation in a hard gelatin capsule by conventional techniques are:

| | |
|---|---|
| Compound of Formula Io, e.g., the compound of Example 5b | 1 mg. |
| Corn starch | 248 mg. |
| Magnesium stearate | 1 mg. |
| Compound of Formula Is, e.g., the compound of Example 5c | 0.5 mg. |
| Corn starch | 248.5 mg. |
| Magnesium stearate | 1 mg. |
| Compound of Formula Is, e.g., the compound of Example 8 (sodium salt) | 0.5 mg. |
| Corn starch | 248.5 mg. |
| Magnesium stearate | 1 mg. |

Salts may be prepared in conventional manner from free acids, lactones and esters and vice-versa. Whilst mono- and polyvalent salts are contemplated by this invention monovalent pharmaceutically acceptable salts especially sodium, potassium and ammonium particularly sodium salts are preferred.

EXEMPLIFICATION

The following examples are illustrative of the invention. All temperatures are centigrade and room temperature (R.T.) is 20° to 30° C., unless indicated otherwise.

Evaporations are done under vacuum (i.v.) employing minimal heating. Drying of organic phases is done over anhydrous sodium sulfate, unless indicated otherwise. THF is tetrahydrofuran, MTBE is methyl tertiary-butyl ether, TTPRD is tris (triphenylphosphonium) ruthenium dichloride and Dibal is diisobutylaluminum hydride. Ether refers to diethyl ether unless indicated otherwise. Paraffin and paraffin oil are also known as mineral oil.

PREPARATION 1

2-tert-butyl-4-(4-fluorophenyl)-5phenyl-3-furylcarboxylic acid, ethyl ester

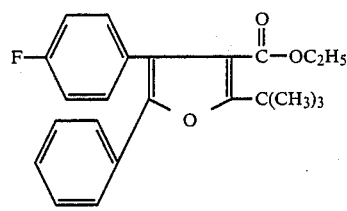

Step 1,

α-bromo-α-(p-fluorophenyl) acetophenone

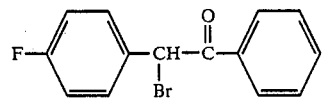

At room temperature, to 20 g (0.093 mol) of α-(p-fluorophenyl)-acetophenone in 200 ml of chloroform, are added a few drops of a charge of 4.8 ml of bromine (0.93 mol) (a deep orange-color results). The resultant solution is heated to initiate reaction (the solution turns yellow), and then cooled to 0° C., and the balance of the 4.8 ml of bromine is added dropwise. The reaction mixture is stirred at room temperature for about 16 hours.

The orange solution is washed three times with saturated aqueous sodium bicarbonate, then once with brine (saturated aqueous sodium choloride), dried, and concentrated to an orange oil, which partially crystallizes.

The product is refined by recrystallization from ethanol yielding refined title product of this step as a white powder (recovered as a first crop of 19.83 g +2.15 g as second crop) for a total of 21.98 g.

Step 2, ethyl 2-(α-benzoyl-4-fluorobenzyl)-3-oxo-4, 4-dimethylpentoate

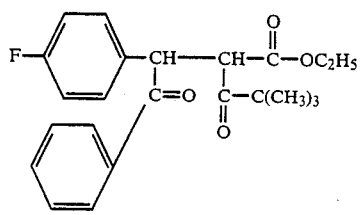

Into a vessel, under a dry nitrogen atmosphere 1.05 g (26.3 m mol) of sodium hydride (60%) in paraffin oil was washed twice with hexane, then suspended in 50 ml of dry THF. 4.3 g (25.1 m mol) of ethyl 4,4-dimethyl-3-oxo-pentoate was added dropwise at 0° C., the reaction mixture was stirred for 15 minutes (resulting in a clear solution). 7.0 g (23.9 m mol) of the bromo product of step 1 of this preparation in 20 ml of THF was added dropwise at 0° C. to the mixture in the flask. The resulting mixture was stirred at room temperature for about 21 hours.

The mixture was then concentrated to obtain a residue. The residue was then taken up in ether, washed twice with saturated aq. sodium bicarbonate solution and then once with brine, dried (over anhyd. magnesium sulfate) and concentrated to crude title product as a yellow oil, which was used directly in the next step (3).

Step 3

2-tert-butyl-4-(4-fluorophenyl)-55-phenyl-3-furylcarboxylic acid, ethyl ester

The crude product of step 2 of this preparation was dissolved in 100 ml. of toluene to which 9 ml (about 3 equivalents) of BF$_3$·O(C$_2$H$_5$)$_2$ was added and the mixture refluxed for 1¼ hours. The reaction mixture was then poured into 150 ml of sat. aq. sodium bicarbonate and extracted twice with 100 ml portions of ether. The combined ether extracts were washed once with brine, dried (over anhyd. magnesium sulfate) and concentrated. The title product of this preparation (brown solid) was recrystallized from ethanol yielding a first crop of 4.88 g and a second crop of 0.68 g, for a total of 5.56 g of refined title product of this preparation, M.P. 93°–94°.

PREPARATION 2

Repeating the procedure of preparation 1 but in step 2, using in place of the ethyl 4,4-dimethyl-3-oxo-pentoate an approximately equivalent amount of ethyl 4-methyl3-oxo-pentoate there is according obtained the 2-isopropyl analog of the product of that preparation (M.P. 69°–70°).

PREPARATION 3

4-(4-fluorophenyl)-2-isopropyl-5phenyl-3-thiophene-carboxylic acid, ethyl ester

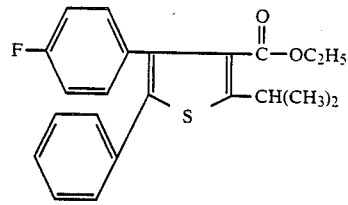

Step 1

α-(4-fluorophenyl-β-mercapto-benzene ethanol

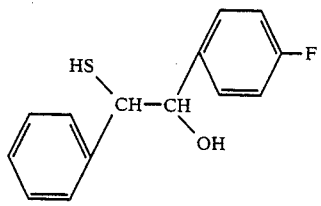

To a solution of 12.4 g (0.1 mole) of benzyl mercaptan (ie, benzenemethanethiol) in 150 ml of THF at 0° C. under moisture-free conditions, was added, dropwise, 14 g (0.22 mole) of n-butyllithium (1.6 m in hexane). After stirring at 0° C. for 4 hours (orange precipitate forms), the mixture was cooled to −25°. To this mixture was added a solution of 12.4 g (0.1 mole) of p-fluorobenzaldehyde in 100 ml of THF, dropwise. After stirring at −25° C. for 1 hour, a yellow solution occurs. The reaction was quenched with saturated aqueous ammonium chloride and the organic material was extracted once with MTBE and then once with methylene chloride. The organic solutions were combined and dried, and the solvent was removed under reduced pressure to give 25 g of the title product of this step as an oil (80:20 mixture of isomers), which was used in the next step without any further purification.

Step 2

2-diethoxyphosphinyl-4-methyl-pent-3-enoic acid, ethyl ester

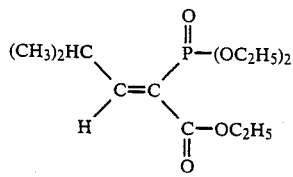

A mixture of 22.4 g (0.1 mole) of triethylphosphonoacetate, 40 g (0.56 mole) of isobutyraldehyde, 3 ml of acetic acid, and 0.6 g of piperidine in 200 ml of benzene was refluxed in a Dean Stark apparatus for 48 hours. The solvent was removed under reduced pressure and the resulting oil was distilled at 0.33 mm to give 28.4 g (100% yield) of product, b.p. 110°–120° C. (product is composed of an isomeric mixture ratio 85:15).

Step 3

2-(diethoxyphosphinyl)-3-[2-(4-fluorophenyl)-2-hydroxy-1-phenylethyl]-thio-4-methyl-pentanoic acid, ethyl ester

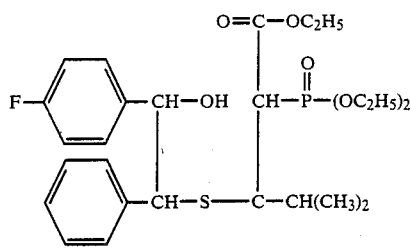

To a solution of 24.8 g (0.1 mole) of the mercapto product of step 1, above, and 28.4 g (0.1 mole) of the ester product of step 2, above, in 300 ml of THF was added 11 g (0.11 mole) of triethylamine. The mixture was then stirred at room temperature for 4 hours. Then the reaction mixture was poured into water and the organic material was extracted once with MTBE and once with methylene chloride. The organic solutions were combined and dried, and the solvent was removed under reduced pressure to give 42 g of the title product of this step, as an oil (mixture or isomers). This was used in the next step (4) without further purification.

Step 4

2-(diethoxyphosphinyl)-3-[2-(4-fluorophenyl)-2-oxo-1-phenylethyl]-thio-4-methyl-pentanoic acid, ethyl ester.

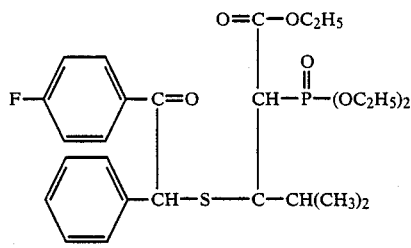

To a solution of 12.2 g (0.096 mole) of oxalyl chloride in 1 liter of methylene chloride at −68° C. was added dropwise a solution of 15 g (0.194 mole) of DMSO in 40 ml of methylene chloride. After stirring at −65° for 5 minutes, a solution of 42 g (0.08 mole) of the product of step 3 in 200 ml of methylene chloride was added dropwise. Stir at −65° C. for 1 hour. Then 40 g (0.4 moles) of triethylamine was added. After allowing the mixture to warm to RT, the mixture was poured into water. The organic phase was separated and the solvent was removed under reduced pressure. The residue was dissolved in MTBE and the solution was washed with water. The organic phase was dried and the solvent was removed under reduced pressure to give 45 g of crude title product of this step as an oil.

Step 5

4-(4-fluorophenyl)-2,5-dihydro-2isopropyl-5-phenyl-3-thiophenecarboxylic acid, ethyl ester

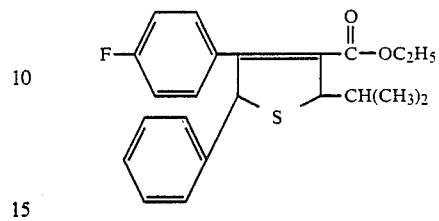

Under essentially moisture-free conditions, to a solution of 8.1 g of diisopropylamine in 500 ml of THF at 0° was added 5.25 g of n-butyllithium (1.6 m in hexane). After stirring at 0° for 5 minutes, a solution of 45 g of the carbonyl product of step 4, above, in 100 ml THF was added rapidly after stirring at room temperature for 1 hour. The mixture was quenched with saturated aqueous ammonium chloride.

The mixture was extracted with MTBE and the organic phase was dried. The solvent was removed under pressure to give 40 g of the title product of this step as an oil, which was used in the next step (6) without further purification.

Step 6

4-(4-fluorophenyl)-2-isopropyl-5-phenyl-3-thiophenecarboxylic acid, ethyl ester

To a suspension of 25 g of 2,3 dichloro-5,6-dicyanobenzoquinone in 1 liter of methylene chloride at room temperature was added slowly a solution of 40 g of the dihydrothiophene carboxylate of Step 5, above, in 125 ml of methylene chloride. The mixture was stirred at room temperature for 24 hours, filtered, and the filtrate was washed with 10% aqueous sodium bicarbonate solution. The organic phase was separated and the solvent was removed under reduced pressure. The residue was filtered through a pad of silica gel to remove any polar material. Evaporation of the solvent gave 41.5 g of the title product of this preparation.

PREPARATION 4

2-Isopropyl-5-(4-chlorophenyl)-4-(4-fluorophenyl)-3-thienylcarboxylic acid, ethyl ester

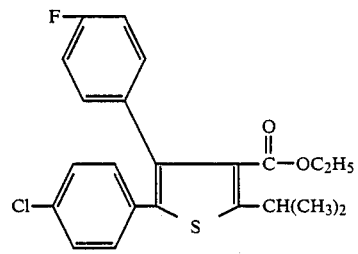

Step 1

4-fluoro-[bis-(methylthio)methylbenzene] (may also be called α,α-di-(methylmercapto)p-fluorotoluene)

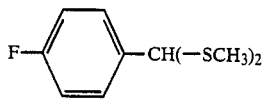

To a mixture of 196 g (1.56 mol) of p-fluorobenzaldehyde and 100 g (3.12 mol) of methanethiol in 1200 ml of ether in a 1 liter 2-neck flask equipped with a dry ice condenser was added, dropwise, 32.16 ml of BF$_3$·O(C$_2$H$_5$)$_2$ at 0° C. The mixture was stirred at 0° C. for 4 hours, then treated with 10% aqueous sodium hydroxide solution and extracted with ether. After drying (over anhydrous magnesium sulfate) and concentration, the product was distilled under reduced pressure to yield 220 g. of the title product of this step; b.p. 120°–122° C.

Step 2

ββ-bis(methylthio)-α-(p-chlorophenyl)
p-fluorobenzeneethanol (may also be called
1-(4-chlorophenyl)-2-(4-fluorophenyl)-2,2-di-(methylmercapto)-ethanol)

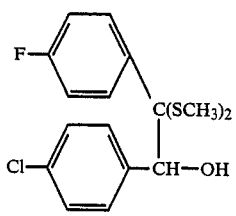

To a stirred solution of 25.0 g (135 mmol) of the dithioacetal product of step 2, above in 200 ml of dry THF at −78° under nitrogen was added 91 ml (140 mmol) of n-butyllithium (1.55M, in hexane solution). After two hours, 18.7 g (140 mmol) of p-chlorobenzaldehyde was added and the mixture was stirred for another hour. The reaction mixture was poured into saturated aqueous ammonium chloride solution, extracted with ether, washed with water, dried over magnesium sulfate, filtered, and concentrated to give 40 g of the crude title product of this step.

Purification by liquid chromatography (Waters Prep 500) gave 28.5 g of refined title product of this step as an oil.

Step 3

α-(4-chlorophenyl)-α-hydroxy-4-fluoroacetophenone

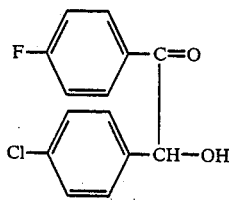

To a mixture of 27 g (78 mmol) of the hydroxydithiolketal product of Step 2, above and 33.8 g (156 mmol) of mercuric oxide (red) in 240 ml of 80% THF was added dropwise 40 ml of BF$_3$·O(C$_2$H$_5$)$_2$. The mixture was stirred at 0° C. for 2 hours, then washed with water, 10% aqueous sodium bicarbonate, then brine and dried over anhydrous magnesium sulfate, and evaporated to dryness to obtain crude title product of this step. Purification by prep LC (Waters Prep 500) on silica gel using hexane-methylene chloride (1:1) gave 14.6 g of refined title product of this step.

Step 4

α-bromo-α-(4-chlorophenyl)-4-fluoroacetophenone

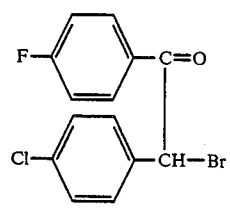

To a mixture of 14.0 g (53 mmol) of the hydroxyketone product of Step 3, above, in 300 ml of THF was added 27.7 g (106 mmol) of carbon tetrabromide, followed by 35 g (106 mmol) of triphenylphosphine. The mixture was stirred at room temperature for 6 hours and filtered. After removal of solvent by evaporation, hexane was added to the residue and the resulting mixture was filtered. The filtrate was concentrated to dryness to obtain crude title product of this step, which was purified by chromatography (Waters Prep 500) yielding 16.2 g of refined product of this step.

Step 5

α-(4-fluorobenzoyl)-4-chlorobenzyl ester of
ethanethioic acid (may also be called
1-fluorobenzoyl-1-(4-chlorophenyl)-methylthio acetate)

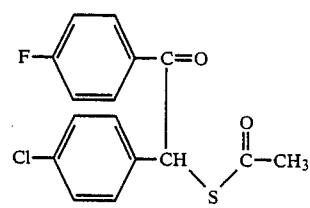

To a stirred solution of 16 g (49 mmol) of the bromoketone product of Step 4, above, in 150 ml of absolute ethanol was added 8.3 g (73.5 mmol) of potassium thioacetate and the suspension was stirred at room temperature for about 16 hours. After removal of the solid by filtration, the solution was washed with water, dried over anhydrous magnesium sulfate, and evaporated to give crude title product of this step as an oil which was refined by chromatographing on silica gel using ethyl acetate-hexane (1:9); to yield: 14 g of refined title product of this step.

Step 6

α-mercapto-α-(4-chlorophenyl)-methyl-4-fluoroacetophenone (may also be called 1-(p-chlorophenyl)-1-(p-fluorobenzoyl)-methylmercaptan)

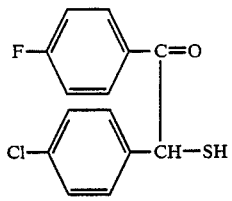

A stirred solution of 9.0 g (31.07 mmol) of the thioacetate product of Step 5, above, in 100 ml of methanol was treated with 2.5 ml of concentrated hydrochloric acid at 0° C. The reaction mixture was heated at 60° C. for 18 hours and concentrated to obtain a residue. The residue was then dissolved in ether and washed with water and then brine. The ethereal solution was dried over anhyd. magnesium sulfate and evaporated to dryness to obtain crude title product of this step. Chromatographing the crude product on silica gel using ethyl acetate-hexane yielded 4.5 g of refined title product of this step.

Step 7

2-isopropyl-5-(4-chlorophenyl)-4-(4-fluorophenyl)-2,5-dihydro-3-thiophenecarboxylic acid, ethyl ester.

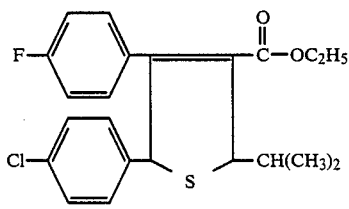

To a stirred solution of 1.73 g (17.1 mmol) of diisopropylamine in 20 ml of dry THF under nitrogen at 0° C. was added 11 ml (17.1 mmol) of n-butyllithium. After 15 minutes, 4.0 g (14.2 mmol) of the mercaptoketone product of Step 6, above, was added dropwise, and the mixture was stirred at −78° for 30 minutes. 4.5 g (14.2 mmol) of ethyl 2-diethoxyphosphinyl-4-methyl-pent-3-enoic acid, (product of Step 2 of Preparation 3, above) was added, and the mixture stirred for 2 hours at −78°. The cooling bath was removed and the solution was allowed to warm to 0° and stirred for two more hours. The mixture was then poured into saturated aqueous ammonium chloride and extracted with ether. The extracts were washed with water, dried over anhydrous magnesium sulfate, filtered, and concentrated to give the crude title product of this step. The crude product was chromatographed on silica gel to yield 4.8 g of refined title product of this step.

Step 8

2-Isopropyl-5-(4-chlorophenyl)-4-(4-fluorophenyl)-3-thienylcarboxylic acid, ethyl ester Repeating the procedure described in Step 6 of Prep. 3, above, but using in place of the 4-(4-fluorophenyl)-2,5-dihydro 2-isopropyl-5-phenyl-3-thiophenecarboxylic acid, ethyl ester product thereof, an approximately equivalent amount of the refined product of Step 7 of this preparation, above, there is accordingly obtained the title product of this preparation.

Adopting the procedure of Preparation 3, the following compounds are analogously obtained, in which $R^2$ is isopropyl and $R^{15}$ is ethyl (in the table: ph=phenyl, Ch=cyclohexyl Cp=cyclopentyl and Me=methyl):

| Preparation No. | $R^1$ | $R^3$ |
| --- | --- | --- |
| 5 | ph | ph |
| 6 | 3-F—ph | ph |
| 7 | Ch | ph |
| 8 | 2-F—ph | ph |
| 9 | Cp | ph |
| 10 | 4-MeOph | ph |
| 11 | 3-CF$_3$—ph | ph |
| 12 | 4-pH—ph | ph |
| 13 | 4-F—ph | 4-MeO—ph |
| 14 | 4-F—ph | 4-Me—ph |

Adopting the procedure of Preparation 4, the compounds of Preparations 5 to 14 above, plus the following compounds may be analogously obtained, in which $R^2$ is isopropyl and $R^{15}$ is ethyl (in the table ph=phenyl; Me=methyl; ip=isopropyl; cp=cyclopentyl and dm=—CH═C(CH$_3$)$_2$):

| Preparation No. | $R^1$ | $R^3$ |
| --- | --- | --- |
| 15 | 4-F—ph | ip |
| 16 | ph | Me |
| 17 | 4-F—ph | cp |
| 18 | 4-F—ph | dm |

EXAMPLE 1

7-[2-tert.-butyl-4-(4-fluorophenyl)-5-phenyl-fur-3-yl]3,5-dihydroxy-hept-6-enoic acid, ethyl ester (*trans*)

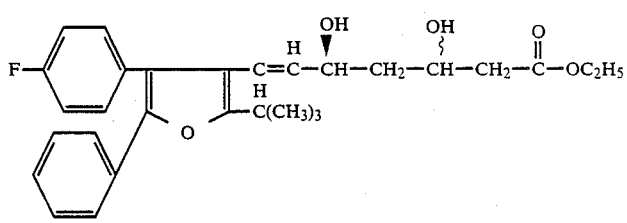

Step 1

2-tert.-butyl-4-(4-fluorophenyl)-5-phenyl-fur-3-ylmethanol

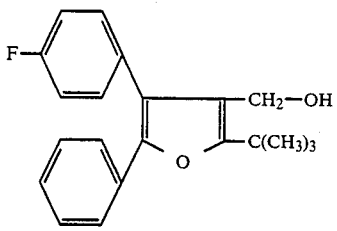

Under a dry nitrogen atmosphere, to a slurry of 1.15 g (30.4 mmol) of lithium aluminum hydride in 50 ml of dry ether at about 0° was added 5.56 g (15.2 mmol) of 4-(4-fluorophenyl)-2-tert.-butyl-5-phenyl-3-furyl-carboxylic acid, ethyl ester in 25 ml of dry ether. The mixture was heated at reflux for one-half hour.

The solution was cooled to 0° C., and quenched with water until a white precipitate persists. The precipitate is filtered off, and washed with ether on the filter plate. The combined washings and the filtrate are dried (over magnesium sulfate) and concentrated to a white solid, which is used directly for the next step (conversion to its aldehyde).

Step 2

2-tert.-butyl-4-(4-fluorophenyl)-5-phenyl-3-furylcarboxaldehyde

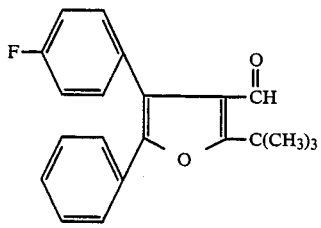

Under a dry nitrogen atmosphere, to a slurry of 583 mg (0.608 mmol) of TTPRD and 3.56 g (30.4 mmol) of NMO (N-methylmorpholine N-oxide) in 50 ml of acetone was added 4.92 g (15.2 mmol) of the alcohol product of Step 1, above, in 10 ml of acetone at room temperature), and the mixture was stirred (at RT) for 2 hours.

The mixture was then concentrated and the resulting black residue taken up in ether. The ether solution was then washed three times with 10% hydrochloric acid, once with saturated aq. sodium bicarbonate, then with brine and dried (over anh. magnesium sulfate and concentrated to a black oil. Upon standing for about 18 hours in the freezer the oil had formed a solid. The solid was recrystallized from ethanol to give a first crop of 2.97 g of a grey powder, and the mother liquor further processed.

Additional product was obtained from the mother liquor by chromatography (silica gel, 25% ether/hexane).

Step 3

3-[2-tert.-butyl-4-(4-fluorophenyl)-5-phenylfur-3-yl]-2-propenal (*trans*)

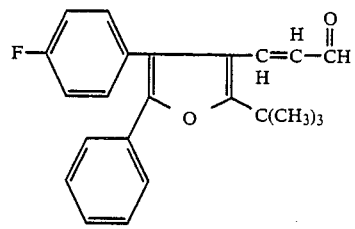

Under an atmosphere of dry nitrogen, 1.56 g (9.3 mmol, 1.10 ml) of *cis*-bromoethoxy ethylene was added to about 20 ml of dry THF and cooled to −78°. 11.0 ml (18.6 mmol) of tert.-butyl lithium was cannulated into a dropping funnel and then added dropwise at −78°. The mixture was stirred for 2 hours at −78°.

2.0 g (6.2 mmol) of the aldehyde product of Step 2, above in about 5 ml of dry THF was added dropwise at −78° and the mixture stirred for 15 minutes (TLC indicated no starting material present). The mixture was then quenched with about 5 ml of saturated aq. ammonium chloride, stirred until the mixture was homogenous, and then extracted twice with 25 ml portions of ether. The combined ether extracts were washed once with brine, dried over anhyd. magnesium sulfate and concentrated to a brown oil. The oil was dissolved in 10% aqueous THF to which toluene sulfonic acid (TSOH) had been added. After stirring for 15 minutes the solution was diluted with saturated aq. sodium bicarbonate, extracted twice with 25 ml portions of ether and the combined ether extracts were washed once with brine, dried over anhydrous magnesium sulfate and concentrated to a brown oil. The oil was dissolved in about 3 ml of ethanol and the solution stored in a freezer. 1.335 g of product of this step was isolated from the reaction mixture as light yellow crystals.

Additional product was recovered by flash chromatography 2:1 (hexane/ether).

Step 4

7-[2-tert.-butyl-4-(4-fluorophenyl)-5-phenylfur-3-yl]-5-hydroxy-3-oxo-hept-6-enoic acid, ethyl ester.

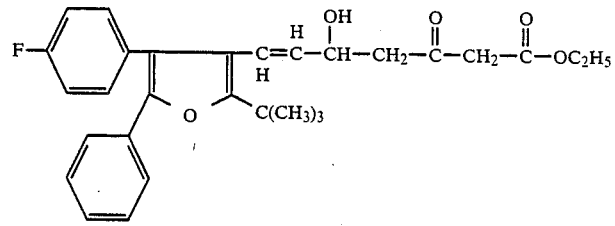

Under a dry nitrogen atmosphere, 398 mg of 60% sodium hydride in paraffin oil (9.96 mmol) is charged to a flask, washed twice with hexane, and then suspended in about 150 ml of dry THF. The mixture is cooled to about −15° (using ice/methanol) and 1.25 g (9.57 mmol) of neat ethyl acetoacetate added thereto, dropwise. The mixture is stirred until it clears (about 15 minutes). 6.30 ml of 1.55 m n-butyl lithium (in hexane) (9.76 mmol) is added by syringe at −15° C. and the mixture stirred for 15 minutes.

1.335 g (3.83 mmol) of the aldehyde product obtainable by the method of Step 3, above, dissolved in about 25 ml of dry THF is added, dropwise at −15° C. The mixture is stirred for 15 minutes, then quenched with water.

The quenched mixture is extracted twice with portions of ether. The ether extracts are combined and washed once with brine, dried over anhydrous magnesium sulfate and concentrated to a yellow oil (crude product of this step). The oil is flash chromatographed (3:2 ether/hexane) to obtain the refined title product of this step as a clear oil.

Step 6

7-[2-tert.-butyl-4-(4-fluorophenyl)-5-phenyl-fur-3-yl]3,5-dihydroxy-hept-6-enoic acid, ethyl ester 379 mg (0.69 mmol) of the refined boron intermediate prepared in Step 5, above, was dissolved in methanol (requiring slight heating) and the solution concentrated on a rotary evaporator (repeating 5 times) to obtain a residue.

The residue was purified by column chromatography (15%) ether-methylene chloride) and concentrated to give 281 mg of final product as a clear oil. The oil was taken up in pentane-ether and crystallized to give 251 mg of refined title product as a white powder. (m.p. 94°-95° C.; 96% erythro diol).

EXAMPLE 2

7-[4-(4-fluorophenyl)-2-isopropyl-5-phenyl-fur-3-yl]-3,5-dihydroxy-hept-6-enoic acid, ethyl ester (*trans*)

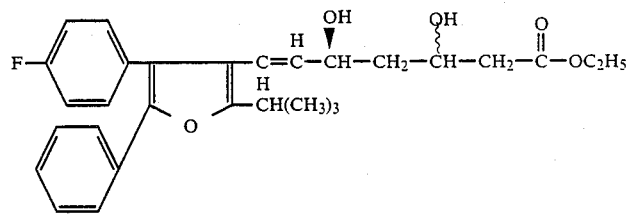

Step 5

Butyl borane complex intermediate

Step 1

4-(4

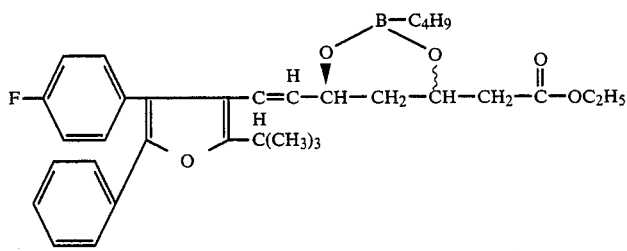

Under a dry nitrogen atmosphere, 890 mg (1.88 mmol) of the oxoheptenoate of Step 4, above, was dissolved in 20 ml of dry THF and 3.75 ml of 1.0M tri-n-butyl borane in THF (3.75 mmol) was added at once. Air was bubbled through the solution for 1 minute and this was allowed to stir (at RT) for 1 hour (yellow mixture). The reaction mixture was cooled to about −55° (using a cryogenic cooler) and 213 mg (5.63 mmol) of sodium borohydride was added at once. The mixture was stirred at −55° for about 65 hours.

The reaction was quenched with about 5 ml of water and extracted twice with 25 ml portions of ether. The combined ether extracts were washed once with brine, dried over anhyd. magnesium sulfate and concentrated to crude product of this step as a yellow oil.

About 3 ml of isopropanol was added to the oil (crude product) and held in a freezer for about 50 hours. 389 g of refined product was isolated as a white powder (m.p. 55°-58°), for use in the next step.

fluorophenyl)2-isopropyl-5-phenyl-3-furylcarboxaldehyde

Following the procedure of Steps 1 and 2 of Example 1, above, but using in place of the 4-(4-fluorophenyl-2-tert.-butyl-5-phenyl-3-furylcarboxylic acid ethyl ester used therein, the 2-isopropyl analog thereof, there is accordingly obtained the title product of this step, m.p. 153°, (white needles).

Step 2

3-[4-(4-fluorophenyl)-2-isopropyl-5-phenyl-fur-3-yl]-prop-2-enoic acid, ethyl ester

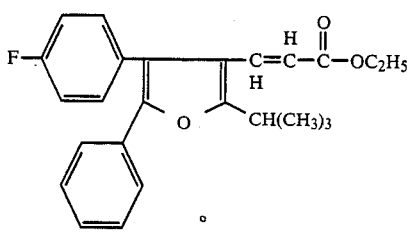

Under essentially moisture-free conditions, 740 mg of 60% sodium hydride in paraffin oil (18.9 mmol) is charged to a vessel and washed three times with hexane. Excess hexane is removed under a stream of dry nitrogen gas. About 25 ml of dry THF is introduced and then 3.95 g (3.3 ml; 17.6 mmol) of triethyl phosphonoacetate. (The first 3-5 drops being added at RT, while the remainder is added at 0°). The mixture is stirred at RT until a clear solution is obtained (about 15 to 30 minutes). 2.71 g (8.8 mmol) of the aldehyde product of Step 1, above, in about 15 ml of dry THF is added, dropwise, at RT. The mixture is stirred for about 24 hours.

The reaction mixture is then concentrated, taken up in ether, the solution washed twice with brine, dried over anhydrous magnesium sulfate, and concentrated. Slow crystallization of the title product of this step occurs on standing in a freezer. The solids are recrystallized from ethanol. 2.57 g of the product (77%) was so obtained as a first crop. m.p. 116°–118° C.

Step 3

3-[4-(4-fluorophenyl)-2-isopropyl-5-phenylfur-3-yl]prop-2-enol

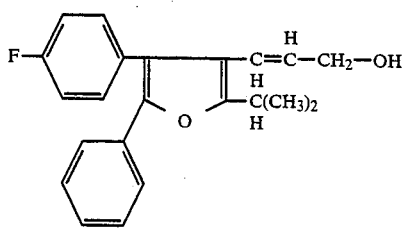

Under a nitrogen atmosphere, 2.57 g (6.8 mmol) of the ester product of Step 2, above, is dissolved in 100 ml of dry ether, and cooled to −78°. 18 ml of 1.5M "Dibal" (27 mmol) is added dropwise. The mixture is stirred at −78° for 15 minutes. The mixture is quenched with excess water (about 5 ml), and stirred at RT for about 45 minutes (until gel separates as a precipitate). The mixture is filtered over a bed of sand, the precipitate washed with ether, the filtrate dried over magnesium sulfate and concentrated to obtain crude title product of this step as a residue, in which form it can be used for the next step (Step 4), described below.

Step 4

3-[4-(4-fluorophenyl)-2-isopropyl-5-phenylfur-3-yl]-2-propenal

Under a nitrogen atmosphere, to a suspension of 4 mg (0.004 mmol) of TTPRD and 30.5 mg (0.26 mmol) of NMO in 15 ml of acetone was added 45 mg (0.13 mmol) of the alcohol product of Step 4, obtained as described above, in 3 ml acetone, at RT. The mixture was stirred for about 18 hours. TLC indicated incomplete consumption of starting material. An additional equivalent of NMO (one half the original amount) and 0.03 equivalent (equal to original amount) of TTPRD was added, and the mixture stirred at RT for one hour.

The mixture was concentrated, to a residue. The residue was taken up in ether, washed three times with 10% hydrochloric acid, sat. aq. sodium bicarbonate and then brine, dried over magnesium sulfate, and concentrated to a brown oil. The oil was passed through a plug of silica (using 25% ether, methylene chloride) and the filtrates concentrated to a yellow solid. The solid was recrystallized from hexane to give 23 mg (53%) of the title product of this step as yellow granules, m.p. 124°–125°.

Repeating the procedure of Steps 4, 5 and 6 of Example 1, above, but using in place of the 2-tertiary butyl propenal product used in Step 4 thereof, an approximately equivalent amount of the 2-isopropyl propenal product of Step 4 of this example, there is accordingly obtained the title product of this example, m.p. 98°–100°, (erythro to threo=87:13).

EXAMPLE 3

7-[4-(4-fluorophenyl)-2-isopropyl-5-phenylthien-3-yl]-3,5-dihydroxy-hept-6-enoic acid, ethyl ester (trans)

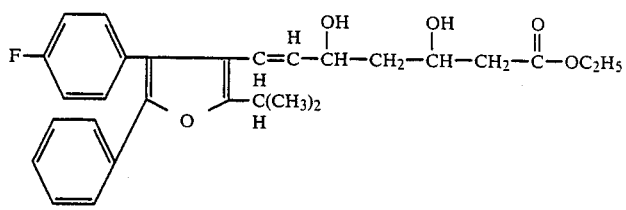

Step 1

4-(4-fluorophenyl)-2-isopropyl-5-phenyl-3-thiophenemethanol

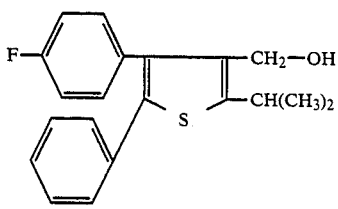

150 ml of a 1.0 m solution of lithium aluminum hydride in THF was diluted with 400 ml of dry THF. To this was added dropwise a solution of 40 g of the title ester product of Preparation 3, above, in 100 ml of THF. After the addition was complete, the reaction was stirred at R.T. for 5 hours. Approximately 10-15 ml of saturated aq. sodium sulfate solution was added dropwise until a thick precipitate formed. The mixture was diluted with MTBE and the solids were filtered and washed well with MTBE. The filtrate was evaporated under reduced pressure to give 18.2 g of crude title product of this step, which was refined by chromatographing on a waters prep-500 apparatus using methylene chloride as eluate, to obtain 10.5 g of refined title product of this step, m.p.=140°-143°.

Step 2

4-(4-fluorophenyl)-2-isopropyl-5-phenyl-thiophenecarboxaldehyde

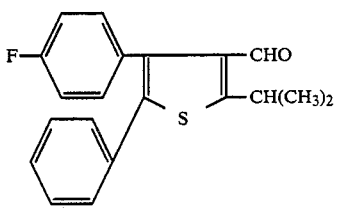

To a solution of 1.92 g of oxalyl chloride in 50 ml of methylene chloride at −78° was added dropwise a solution of 2.22 g of dimethylsulfoxide in 25 ml methylene chloride. After stirring at −78° for 10 minutes, a solution of 4.0 g of the title methanol product of Step 1, above, in 30 ml of methylene chloride was added dropwise. The mixture was stirred at −78° for 1 hour. Then 2.5 g of triethylamine was added. The mixture was allowed to warm to R.T., then was poured into water. The organic phase was separated and the solvent was removed under reduced pressure. The residue was dissolved in MTBE and washed with water. The organic solution was dried, and the solvent was removed under reduced pressure to give 3.8 g or the title product of this step. A sample of which was triturated with pentane to give refined product. M.P. 116°-120°.

Step 3

3-[4-(4-fluorophenyl)-2-isopropyl-5-phenythien-3-yl]-2-propenal (*trans*)

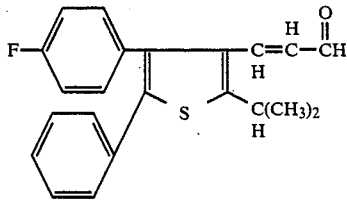

To a solution of 2.4 g of *cis*-2-bromo-ethoxyethylene in 75 ml of THF at −78°, was added dropwise 2.0 g of t-butyllithium (2.2 m in pentane). After stirring at −78° for 2 hours, a solution of 3.5 g of the aldehyde product of Step 2, above, in 30 ml of THF was added dropwise. The reaction was stirred at −78° for 10 minutes, then was quenched by the addition of saturated aq. ammonium chloride solution. The mixture was extracted once with MTBE and then once with methylene chloride. The organic solutions were combined, dried over anhyd. magnesium sulfate and concentrated under reduced pressure to obtain a residue. The residue was dissolved in 100 ml of THF/water (90:10). p-toluenesulfonic acid (0.7 g) was added and then the mixture was stirred at room temperature for 1 hour. The reaction mixture was poured into 10% aq. sodium bicarbonate solution and the organic material was extracted with MTBE. The solution was dried and the solvent removed under reduced pressure to give 3.7 g (98% yield) of the title product of this step for use in the next step (4). An analytical sample was crystallized from hexane; m.p. 138°-140°;

Step 4

7-[4-(4-fluorophenyl)-2-isopropyl-5-phenylthien-3-yl]-5-hydroxy-3-oxo-hept-6-enoic acid, ethyl ester (*trans*)

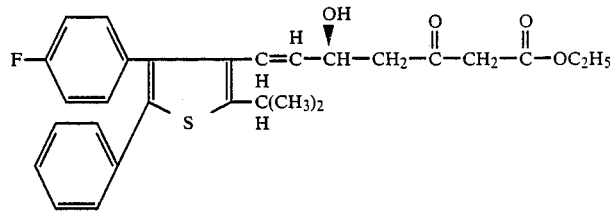

To a solution of 2.6 g of diisopropylamine in 30 ml of THF at 0° was added 1.67 g of n-butyllithium (1.16 m in hexane). Then a solution of 1.7 g of ethyl acetoacetate in 10 ml of THF was added dropwise. After stirring at 0° for 1 hour, the mixture was cooled to −20°, then a solution of 3.3 g of the title product of Step 3, above, in 20 ml of THF was added dropwise. The reaction was stirred at −20° for 1 hour. Then was quenched with saturated aqueous ammonium chloride solution. The mixture was extracted with MTBE and then methylene chloride and the organic solutions were combined and dried, adn the solvent evaporated under reduced pressure to give 5.5 g of crude title product of this step as an oil. This was used without further purification in the next step (Step 5).

Step 5

7-[4-(4-fluorophenyl)-2-isopropyl-5-phenylthien-3-yl]-3,5-dihydroxy-hept-6-enoic acid, ethyl ester (*trans*)

To a solution of 5.5 g of the title product of Step 4, above, in 100 ml of THF was added 12 ml of a 1.0 m solution of triethylborane in THF. After stirring at R.T. for 3 hours, the mixture was cooled to −78°, then 450 mg of sodium borohydride was added. The mixture was stirred at −78° for 24 hours. The reaction was then quenched with saturated aq. ammonium chloride solution, and extracted twice with MTBE. The extracts were combined and solvent was removed under reduced pressure to obtain a residue. The residue dissolved in 100 ml of methanol. After stirring at R.T. for 24 hours, the solvent was removed under reduced pressure and the resulting residue was flash chromatographed using 1% methanol/methylene chloride to elute the product, yielding 2.4 g of the title product of this example. (HPLC indicated an erythro:threo mixture of 82.3:17.7). Recrystallization of the product from cyclohexane increased the ratio to 88.3:11.7; m.p.=123°–125°.

EXAMPLE 3A (E)-7-(4-phenyl-2-isopropyl-5-phenylthien-3-yl)-3,5-dihydroxy-hept-6-enoic acid, ethyl ester.

Repeating the procedure of Examples 1, 2 or 3, but using as compound A the product of Preparation 5, above, there is accordingly obtained the title ester product, M.P. 105°–6°.

EXAMPLE 4

Sodium 7-[4-(4-fluorophenyl)-2-isopropyl-5-phenylthien-3-yl]-3,5-dihydroxy-hept-6-enoate (trans)

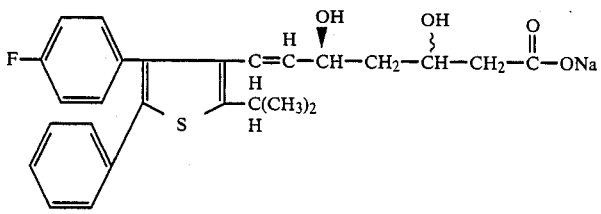

To a solution of 482 mg of the title product of Example 3 in 25 ml of ethanol was added 1.0 ml of 1.0N NaOH sodium hydroxide. After stirring at 50° for 2 hours, the solvent was removed under reduced pressure. The residue was dissolved in water and the solution was washed with MTBE. The aqueous phase was separated and lyophilized to give 480 mg of the title product of this example. M.P. 247°–250° (dec).

EXAMPLE 5

Repeating the procedure of Example 4, above, using in place of the ester product of Example 3 employed therein, an approximately equivalent amount of:
(a) the ester product of Example 1;
(b) the ester product of Example 2; or
(c) the ester product of Example 3A; there is accordingly obtained; respectively:
 (a) sodium(E)-7-[2-tert.butyl-4-(4-fluorophenyl)-5-phenyl-fur-3-yl]3,5-dihydroxy-hept-6-enoate (mp 221°–227°);
 (b) sodium(E)-7-[4-(4-fluorophenyl-2-isopropyl-5-phenylfur-3-yl]-hept-6-enoate (mp 221°–229°).
 (c) sodium(E)-7-(4-phenyl-2-isopropyl-5-phenyl-thien-3-yl)-3,5-dihydroxy-hept-6-enoate (mp over 220°, dec.).

Adapting the procedure of Examples 1 to 4, (the following compounds Ia are obtained in which X=S; $R^2$ is isopropyl; Y=a); and $R^{15}$ is ethyl (the erythro isomer predominating about 4:1); (in the Table, me=-methyl, ip=isopropyl, cp=cyclopentyl, and ch=cyclohexyl, d=decomposition, ph=phenyl, and dm=—CH=C(CH$_3$)$_2$):

| Example No. | $R^1$ | $R^3$ | M.P.° etc. of: Ester | Na—Salt |
|---|---|---|---|---|
| 6 | 4-F—ph | 4-Me—ph | 121-2 | 215-20(d) |
| 7 | 4-F—ph | 4-Cl—ph | 130-1 | 210-6(d) |
| 8 | 4-F—ph | ip | 93.5-94 | 220-230(d) |

-continued

| Example No. | $R^1$ | $R^3$ | M.P.° etc. of: Ester | Na—Salt |
|---|---|---|---|---|
| 9 | 4-F—ph | 4-MeO—ph | 97-9 | 116-121(d) |
| 10 | 3-F—ph | ph | 103-4 | |
| 11 | ph | Me | oil | 204-7(d) |
| 12 | ch | ph | oil | 230-5 |
| 13 | 2-F—ph | ph | oil | 208-10 |
| 14 | cp | ph | oil | 220-5(d) |
| 15 | 4-MeOph | ph | oil | 211-6 |
| 16 | 3-CF$_3$—ph | ph | gum | d |
| 17 | 4-ph-ph | ph | 61-4 | 235(d) |
| 18 | 4-F—ph | cp | 97-8 | oil |
| 19 | 4-F—ph | dm | 146-8 | oil |

Upon acidifying the sodium salts of the compounds of Examples 1 to 19 to form the corresponding free acids (compounds Ia$^3$) and applying the procedure of process m, described above, the corresponding lactones thereof (compounds Ib) are obtained.

EXAMPLE 20

7-[4-(4-fluorophenyl)-2isopropyl-5-phenylthien-3-yl]-3,5-dihydroxy-hept-6-anoic acid, ethyl ester A solution of 258 mg of the product of Example 3, above, in 3 ml of ethanol was hydrogenated over 50 mg of palladium on carbon (10%) at 50 psi for 48 hours. The catalyst was removed by filtration and the filtrate evaporated to dryness to give the title product as an oil.

EXAMPLE 21

7-[4-(4-fluorophenyl)-2-isopropyl-5-phenylthien-3-yl]-3,5-dihydroxy-hept-6-anoic acid, ethyl ester A solution of 258 mg of the product of Example 3, above, in 3 ml of ethanol was hydrogenated over 50 mg of palladium on carbon (10%) at 50 psi for 48 hours. The catalyst was removed by filtration and the filtrate evaporated to dryness to give the title product as an oil.

EXAMPLE 21

7-[4-(4-fluorophenyl)-2-isopropyl-5-phenylthien-3-yl]-3,5-dihydroxy-hept-6-anoic acid, sodium salt Treating the product of Example 20, above, by the method of Example 4, there is accordingly obtained the title product of this example, as an oil.

What is claimed is:
1. A compound of the formula:

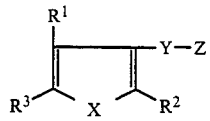

wherein $R^1$ is $C_{1-6}$alkyl not containing an asymmetric carbon atom, $C_{3-7}$cycloalkyl or ring A

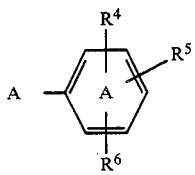

wherein R⁴, R⁵ and R⁶ are as defined below,
R² is C₁₋₆alkyl not containing an asymmetric carbon atom, C₃₋₇cycloalkyl or ring B:

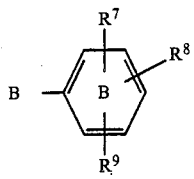

wherein R⁷, R⁸ and R⁹ are as defined below,
R³ is hydrogen, C₁₋₆alkyl not containing an asymmetric carbon atom, C₃₋₇cycloalkyl or ring C:

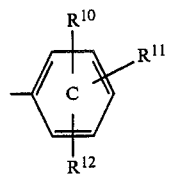

wherein R¹⁰, R¹¹ and R¹² are as defined below;
Y is (a)

or (b) —CH₂—CH₂—;
X is —S—; Z is

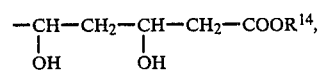

wherein R¹⁴ is hydrogen, R¹⁵ or M,
wherein
R¹⁵ is a physiologically acceptable ester group, and
M is a pharmaceutically acceptable cation,
wherein each of R⁴, R⁷ and R¹⁰ is independently hydrogen, C₁₋₃alkyl, n-butyl, i-butyl, t-butyl, C₁₋₃alkoxy, n-butoxy, i-butoxy, trifluoromethyl, fluoro, chloro, phenyl, phenoxy or benzyloxy,
each of R⁵, R⁸ and R¹¹ is independently hydrogen, C₁₋₃alkyl, C₁₋₃alkoxy, trifluoromethyl, fluoro, chloro, phenoxy or benzyloxy, and
each of R⁶, R⁹ and R¹² is independently hydrogen, C₁₋₂alkyl, C₁₋₂alkoxy, fluoro or chloro, with the provisos that not more than one substituent on each of Rings A, B and C independently is trifluoromethyl, not more than one substituent on each of Rings A, B and C independently is phenoxy and not more than one substituent on each of Rings A, B and C independently is benzyloxy.

2. A compound of claim 1 in which Y is

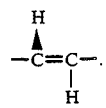

3. A compound of claim 2 in which R¹⁴ is R¹⁵ as defined.
4. A compound of claim 2 in which R¹⁴ is M.
5. A compound of claim 1 in which R¹⁴ is hydrogen.
6. A compound of claim 1 in which R² is alkyl.
7. A compound of claim 6 in which R² is isopropyl.
8. A compound of claim 1 in which R¹ or R² is phenyl.
9. A compound of claim 1 in which R¹ is p-fluorophenyl.
10. The compound of claim 1 which is sodium(E)-7-(4-phenyl-2-isopropyl-5-phenylthien-3-yl)-3,5-dihydroxy-hept-6-enoate.
11. A compound according to claim 1 which is sodium (E)-7-[4-(4-fluorophenyl)-2-isopropyl-5-phenylthien-3-yl]-3,5-dihydroxyhept-6-enoate.
12. A composition useful for treating atherosclerosis in a mammal in need of such treatment comprising an effective amount of a compound of claim 1 and an inert non-toxic, pharmaceutically acceptable carrier, the amount of compound, being an amount effective for inhibiting cholesterol biosynthesis in a mammal.
13. A composition of claim 12 in which the compound is sodium(E-7-(4-phenyl-2-isopropyl-5-phenylthien-3-yl)-3,5-dihydroxyhept-6-enoate.
14. A method of treating atherosclerosis by inhibiting cholesterol biosynthesis comprising administering to a mammal in need of such treatment an amount effective for inhibiting cholesterol biosynthesis of a compound of claim 1.
15. A compound of the formula:

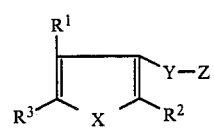

wherein R¹ is C₁₋₆alkyl not containing an asymmetric carbon atom, C₃₋₇ cycloalkyl or ring A

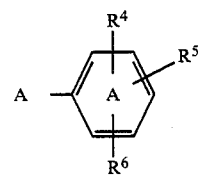

wherein R⁴, R⁵ and R⁶ are as defined below, R² is C₁₋₆alkyl not containing an asymmetric carbon atom, C₃₋₇cycloalkyl or ring B:

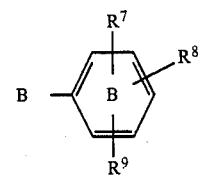

wherein $R^{14}$ is hydrogen, $R^{15}$ or M, wherein $R^{15}$ is a physiologically acceptable ester group, and M is a pharmaceutically acceptable cation, wherein each of $R^4$, $R^7$ and $R^{10}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy, each of $R^5$, $R^8$ and $R^{11}$ is independently hydrogen, $C_{1-3}$alkyl, $C_{1-3}$alkoxy, trifluoromethyl, fluoro, chloro, phenoxy or benzyloxy and each of $R^6$, $R^9$ and $R^{12}$ is independently hydrogen, $C_{1-2}$alkyl, $C_{1-2}$alkoxy, fluoro or chloro, with the provisos that not more than one substituent on each of Rings A, B and C independently is trifluoromethyl, not more than one substituent on each of Rings A, B and C independently is phenoxy, and not more than one substituent on each of Rings A, B and C independently is benzyloxy wherein $R^7$, $R^8$ and $R^9$ are as defined below, $R^3$ is hydrogen, $C_{1-6}$alkyl not containing an asymmetric carbon atom, $C_{3-7}$cycloalkyl,

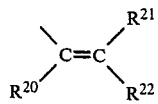

or ring C:

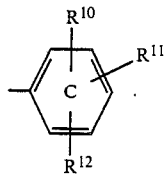

wherein $R^{20}$ is hydrogen or $C_{1-3}$alkyl, each of $R^{21}$ and $R^{22}$ is independently hydrogen, $C_{1-3}$alkyl or phenyl, and $R^{10}$, $R^{11}$ and $R^{12}$ are as defined above with the proviso that $R^3$ may be

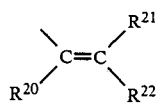

only when Y is (a);

Y is (a)

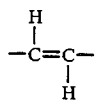

or (b) —CH$_2$—CH$_2$—;

X is —S—;

Z is

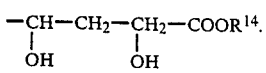

* * * * *